US010982191B2

(12) United States Patent
Voldborg et al.

(10) Patent No.: US 10,982,191 B2
(45) Date of Patent: Apr. 20, 2021

(54) ENGINEERED MAMMALIAN CELLS FOR PRODUCTION OF RECOMBINANT PROTEINS

(71) Applicants: DANMARKS TEKNISKE UNIVERSITET, Lyngby (DK); THE REGENTS OF THE UNIVERSITY OF CALIFORNIA, Oakland, CA (US)

(72) Inventors: Bjørn Gunnar Voldborg, Hillerød (DK); Lasse Ebdrup Pedersen, Copenhagen (DK); Bernhard Palsson, San Diego, CA (US)

(73) Assignees: DANMARKS TEKNISKE UNIVERSITET, Lyngby (DK); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/095,975

(22) PCT Filed: Apr. 25, 2017

(86) PCT No.: PCT/EP2017/059719
§ 371 (c)(1),
(2) Date: Oct. 24, 2018

(87) PCT Pub. No.: WO2017/186671
PCT Pub. Date: Nov. 2, 2017

(65) Prior Publication Data
US 2019/0136198 A1 May 9, 2019

(30) Foreign Application Priority Data

Apr. 25, 2016 (EP) .................................. 16166789

(51) Int. Cl.
*C12N 5/071* (2010.01)
*C12N 9/64* (2006.01)
*C12N 15/113* (2010.01)
*C12N 15/62* (2006.01)
*C12N 15/79* (2006.01)

(52) U.S. Cl.
CPC ......... *C12N 5/0682* (2013.01); *C12N 9/6413* (2013.01); *C12N 15/113* (2013.01); *C12N 15/62* (2013.01); *C12N 15/79* (2013.01); *C12N 2510/02* (2013.01)

(58) Field of Classification Search
None
See application file for complete search history.

(56) References Cited

FOREIGN PATENT DOCUMENTS

| WO | WO 2012/082509 A2 | 6/2012 |
| WO | WO 2012/082509 A3 | 6/2012 |
| WO | WO 2007/006808 A1 | 1/2017 |

OTHER PUBLICATIONS

Baycin-Hizal et al., "Proteomic Analysis of Chinese Hamster Ovary Cells", Journal Proteome Res 2012; 11(11): 5265-5276.
Chaudhuri et al., "Investigation of CHO Secretome: Potential Way to Improve Recombinant Protein Production from Bioprocess", J Bioprocess Biotech 2015; 5:7.
Datta et al., "An Omics Approach Towards Cell Engineering", CHO Biotechnol Bioeng 2013, 110(5):1255-1271.
Kim et al., "CHO cells in biotechnology for production of recombinant proteins: current state and further potential", Appl Microbiol Biotechnol 2012, 93:917-930.
Slade et al., "Identifying the CHO Secretome using Mucin-type O-Linked Glycosylation and Click-chemistry", Journal of Proteome Res 2012, 11:6175-6186.
Zhang, "Mammalian Cell Culture for Biopharmaceutical production", In: Manual of Industrial Microbiology and Biotechnology, Edition: 3rd ed., Chapter: 12, Publisher: ASM Press, Washington, DC., pp. 157-178 (2010).
Lee et al., "CRISPR/Cas9-mediated genome engineering of CHO cell factories: Application and perspectives", Biotechnology Journal 2015, 10(7): 979-994.
Walsh, "Monoclonal antibodies continue their march on the markets, optimized so-called biobetter versions of existing biologics are also gaining ground, but the rate of biosimilar approvals has seen a dramatic slowdown", Nature Biotechnology, 2014, vol. 32 No. 10: 992-1000.
Valente et al., "Expression of Difficult-toRemove Host Cell . . . ", Biotechnology and Bioengineering, vol. 112, No. 6, Jun. 2015.
Hogwood et al., "Host cell protein dynamics in recombinant CHO cells", Bioengineered vol. 4, Issue 5, pp. 288-291, Sep./Oct. 2013.
Kumar, "Host Cell Proteins: the Uninvited Guests in your Biologics Preparation", Enzo Life Sciences, 2015.
International Search Report and Written Opinion issued in PCT/EP2017/059719, dated Oct. 5, 2017, pp. 1-24, European Patent Office.

*Primary Examiner* — Iqbal H Chowdhury
(74) *Attorney, Agent, or Firm* — Marshall, Gerstein & Borun LLP

(57) ABSTRACT

The present invention relates to mammalian cells modified to provide for improved expression of a recombinant protein of interest. In particular, the invention relates to CHO cells and other host cells in which the expression of one or more endogenous secreted proteins has been disrupted, as well as to the preparation, identification and use of such cells in the production of recombinant proteins.

12 Claims, 2 Drawing Sheets
Specification includes a Sequence Listing.

ENGINEERED MAMMALIAN CELLS FOR PRODUCTION OF RECOMBINANT PROTEINS

FIELD OF THE INVENTION

The present invention relates to mammalian cells modified to provide for improved expression of a recombinant protein of interest. In particular, the invention relates to CHO cells and other host cells in which the expression of one or more endogenous secreted proteins has been disrupted, as well as to the preparation, identification and use of such cells in the production of recombinant proteins.

BACKGROUND OF THE INVENTION

Chinese hamster ovary (CHO) cells are the primary expression system for manufacturing biopharmaceuticals, accounting for 35.5% of the total cumulative (1982-2014) biopharmaceutical product approvals (Walsh, 2014). Because of their importance in commercial production of therapeutic recombinant proteins, significant efforts have been made in order to characterize and optimize CHO cells for this purpose (Kim et al., 2012; Datta et al., 2013; Lee et al., 2015; Chaudhuri et al., 2015). These include studies of the CHO cell proteome and secretome, the latter representing the Host Cell Proteins (HCPs) secreted from CHO cells (Baycin-Hizal et al., 2012; Slade et al., 2012; Zhang, 2010).

WO 2007/006808 A1 relates to CHO cells with knocked-down or knocked-out genes encoding host cell proteins contaminating recombinant production of vitamin K-dependent proteins. For example, endogenous Protein S was reported to contaminate preparations of recombinant Factor VIIa, when this protein was produced in CHO cells.

WO 2012/082509 A2 relates to knockdown or knockout of the biomarkers Acsl3, Akr1b8, Anapc10, Arl6ip1, Cnih2, Ctsd, Ctsl, Derl1, Dse, Ebpl, Ecm1, Elk3, Fth1, Gjb3, Hmox1, Itgb1bp1, Ldha, Lgals1, Lgals3, Lrpap1, Myl6b, Pit1, Pomp, Rps26, Sen2, Sh2d3c, S100a4, Tmed1, Tnfrsf12a, Tinagl, Tnfrsf25, Trappc6b, 0610007C21Rik and 2610209M04Rik for the purpose of improving cell growth or viability, and enhancing protein production in CHO cells.

Despite these and other advances in the art, there is still a need for host cells such as CHO cells which are capable of high-yield production of recombinant proteins of interest.

SUMMARY OF THE INVENTION

It has been found by the present inventor(s) that mammalian host cells may be modified, such as by disruption by knockout of specific endogenous genes, for improved or higher expression of a recombinant protein of interest being produced by the host cell, such as a CHO cell.

First of all a production by the mammalian cells of these host cell proteins may be limiting the cells ability to produce a recombinant protein of interest, simply by the use of the same protein production machinery of the cell, or by the supply of nutrients for the proteins. By knocking out these endogenous genes, the host cell do not spend resources on the production of these endogenous proteins product of these genes.

Secondly, some of these endogenous proteins product may be very difficult to completely remove from a media of a host cell producing one or more of these host cell proteins in addition to a recombinant protein of interest.

Another object of embodiments of the present invention is to provide mammalian host cells, which cells are able to grow to a higher cell density. This has a significant advantage in that a higher production of a recombinant protein may be obtained by having more cells in the same batch producing such a recombinant protein.

So, in a first aspect the present invention relates to a mammalian cell, such as a human cell, or in particular a CHO cell modified to disrupt expression of one or more endogenous proteins selected from the group consisting of TIMP1, NID1-1, NID1-2, BGN, CTSD and LGALS3BP.

In a second aspect the present invention relates to a method of producing a recombinant protein of interest, comprising
(a) culturing the CHO cell of claim 9 in a culture medium such that the protein of interest is expressed from the nucleic acid sequence;
(b) harvesting the recombinant protein of interest from the culture medium; and
(c) optionally, further purifying the harvested recombinant protein of interest.

In a third aspect the present invention relates to a method for preparing the CHO cell of the invention, comprising the steps of
(a) modifying the CHO cell to knock-down or knock-out the endogenous gene or genes encoding one or more of TIMP1, NID1-1, NID1-2, BGN, and LGALS3BP; and
(b) optionally, transfecting the modified CHO cell with a nucleic acid sequence encoding a protein of interest.

In a further aspect the present invention relates to a method for preparing a eukaryotic host cell line modified to produce higher levels of a recombinant protein of interest, to increase cell-density, or both, comprising the steps of
(a) determining the at least 6 endogenous secreted proteins of the eukaryotic host cell line which are most abundantly present in the culture medium as determined by mass spectrometry; and
(b) knocking-down or knocking-out the host cell genes encoding the 6 most abundantly secreted endogenous proteins;
wherein the method further comprises a step of transfecting the host cell with a nucleic acid sequence encoding a recombinant protein of interest either before, during or after steps (a) and (b).

In a further aspect the present invention relates to a modified host cell prepared by any of the methods of the invention.

In a further aspect the present invention relates to a kit comprising at least one vector comprising a nucleic acid sequence operatively joined to at least one expression control sequence, wherein the nucleic acid sequence or its transcription product disrupts the expression of one or more endogenous proteins selected from the group consisting of TIMP1, NID1-1, NID1-2 and LGALS3BP when transfected into in a CHO cell.

DETAILED DISCLOSURE OF THE INVENTION

Figure 1:
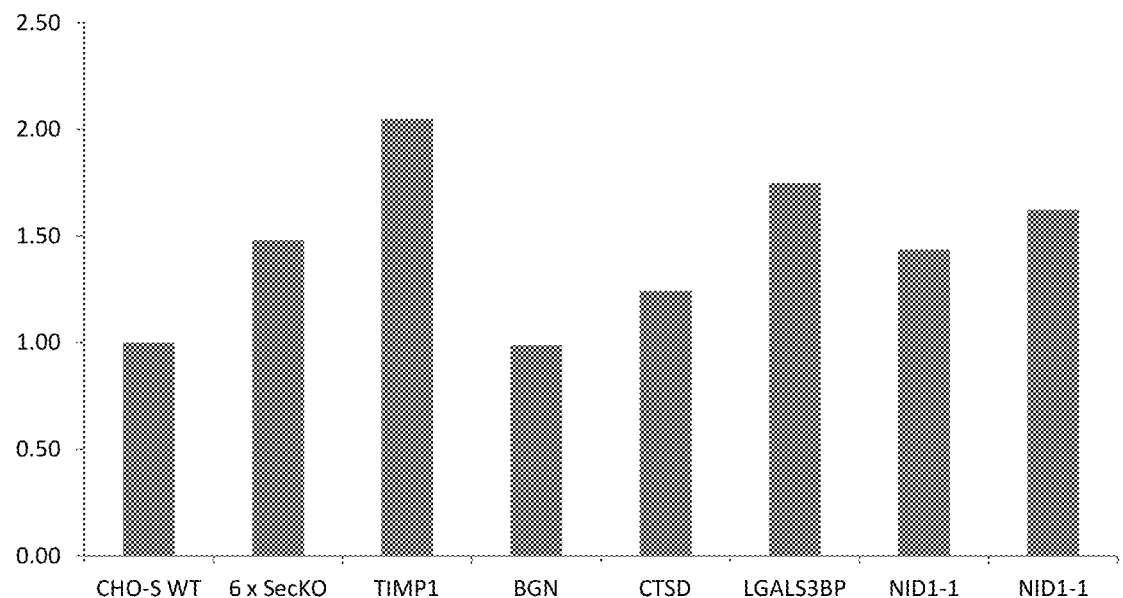
FIG. 1: Rituximab expression from a multiplex secretory KO and individual secretory KO clones (normalized to CHO-S WT). Rituximab titers from transiently transfected CHO cell lines grown in shakerflasks. All titers are normalised to titers from wt CHO cells.

The present invention relates to mammalian cells and in particular CHO cells modified to provide for improved expression of a recombinant protein of interest. In particular, the expression of one or more endogenous secreted proteins has been significantly reduced or disrupted.

It will be understood that in principle any method or technique for reducing or disrupting the expression of one or more endogenous secreted proteins may be used. The examples of such methods including siRNA targeting, targeted gene knock-out, transfection with a transcriptional factor, and site-specific cleavage of the DNA strands encoding protein contaminants are not to be construed limiting in any way. In principle, any molecular biology, cell biology, or selection method may be used to reduce or disrupt the expression level of particular endogenous secreted proteins.

Definitions

The term "disrupt" as used herein refers to the significant reduction to complete removal of the expression of one or more endogenous proteins in a CHO cell, such as be knockdown or knockout. This may be measured as presence of this one or more endogenous proteins in a culture medium of the CHO cell, such as by mass spectrometry wherein the total content of a endogenous protein may be less than at the most 500 ppm, such as at the most 100 ppm, such as at the most 10 ppm, e.g. at the most 1 ppm, or at the most 0.1 ppm, or non-detectable.

The term "knock-down", "reduction" or "depletion" in the context of gene expression as used herein refers to experimental approaches leading to reduced expression of a given gene compared to expression in a control cell. Knockdown of a gene can be achieved by various experimental means such as introducing nucleic acid molecules into the cell which hybridize with parts of the gene's mRNA leading to its degradation (e.g. shRNAs, RNAi, miRNAs) or altering the sequence of the gene in a way that leads to reduced transcription, reduced mRNA stability or diminished mRNA translation.

A complete inhibition of expression of a given gene is referred to as "knock-out". Knockout of a gene means that no functional transcripts are synthesized from said gene leading to a loss of function normally provided by this gene. Gene knock-out is achieved by altering the DNA sequence leading to disruption or deletion of the gene or its regulatory sequences. Knock-out technologies include the use of homologous recombination techniques to replace, interrupt or delete crucial parts or the entire gene sequence or the use of DNA-modifying enzymes such as zink-finger nucleases to introduce double strand breaks into DNA of the target gene.

One specific method for knocking out a specific gene according to the invention is the CRISPR-Cas9 methods as described in e.g. Ronda, Carlotta; Pedersen, Lasse Ebdrup; Hansen, Henning Gram; Kallehauge, Thomas Beuchert; Betenbaugh, Michael J; Nielsen, Alex Toftgaard; Kildegaard, Helene Faustrup; Accelerating genome editing in CHO cells using CRISPR Cas9 and CRISPy, a web-based target finding tool, Biotechnology and bioengineering, 111, 8, 1604-1616, 2014, or in Grav, Lise Marie; Lee, Jae Seong; Gerling, Signe; Kallehauge, Thomas Beuchert; Hansen, Anders Holmgaard; Kol, Stefan; Lee, Gyun Min; Pedersen, Lasse Ebdrup; Kildegaard, Helene Faustrup; One-step generation of triple knockout CHO cell lines using CRISPR/Cas9 and fluorescent enrichment, Biotechnology journal, 2015.

The term "eukaryotic host cell line" as used herein refers to any suitable cell line from eukaryotic origin that can be used for the expression of recombinant proteins. Non-limiting examples of suitable host cell lines includes CHO cells, BKH cells, HKBI I cells, SP2/0 cells, and NSO cells, L-M cells (ATCC CCL 1), HEK293 cells (ATCC CCL 1555), HEK293 (ATCC CRL 1573; Graham et al., J. Gen. Virol. 36: 59-72, 1977), CV-1 cells (ATCC CCL 70), COS-1 cells (ATCC CRL 1650), COS-7 cells (ATCC CRL 1651), 3T3 cells (ATCC CCL 92), NIH/3T3 cells (ATCC CRL 1658), HeLa cells (ATCC CCL 2), C127I cells (ATCC CRL 1616), BS-C-1 cells (ATCC CCL 26) and MRC-5 cells (ATCC CCL 171). One particular suitable cell is a CHO cell (e. g., ATCC CCL 61), such as one selected from a CHO-K1, CHO-S and CHO DG44 cells.

The term "Protein of interest" as used herein refers to any protein that may be produced by recombinant means, typically a protein that require expression in a eukaryotic host cell due to post translational modifications including glycosylation. This includes proteins of human and animal origin, but also proteins of other sources such as plants, insects, etc., and mutated, artificial, synthetic, fusion or chimeric proteins. In particular "protein of interest" includes plasma proteins, peptide hormones, growth factors, cytokines and antibodies. In more detail, plasma proteins include human and animal blood clotting factors such as fibrinogen, prothrombin, thrombin, FX, FXa, FIX, FIXa, FVII, FVIIa, FVIII, FVIIIa, FXI, FXIa, FXII, FXIIa, FXIII, FXIIIa, von Willebrand factor etc., transport proteins such as albumin, transferrin, ceruloplasmin, haptoglobin, hemoglobin, hemopexin, etc., protease inhibitors such as β-antithrombin, α-antithrombin, α2-macroglobulin, CI-inhibitor, tissue factor pathway inhibitor (TFPI), heparin cofactor II, protein C inhibitor (PAI-3), Protein C, Protein S, etc., antiangionetic proteins such as latent-antithrombin, etc., highly glycosylated proteins including alfa-1-acid glycoprotein, antichymotrypsin, inter-α-trypsin inhibitor, α-2-HS glycoprotein, C-reactive protein, etc. and other proteins such as histidine-rich glycoprotein, mannan binding lectin, C4-binding protein, fibronectin, GC-globulin, plasminogen, blood factors such as erythropoeitin, interferon, tumor factors, tPA, gCSF and derivatives and muteins thereof. The antibody may be any therapeutic antibody selected from the group consisting of abagovomab, adalimumab, alemtuzumab, aurograb, bapineuzumab, basiliximab, belimumab, bevacizumab, briakinumab, canakinumab, catumaxomab, certolizumab pegol, cetuximab, daclizumab, denosumab, efalizumab, galiximab, gemtuzumab ozogamicin, golimumab, ibritumomab tiuxetan, infliximab, ipilimumab, lumiliximab, mepolizumab, motavizumab, muromonab, mycograb, natalizumab, nimotuzumab, ocrelizumab, ofatumumab, omalizumab, palivizumab, panitumumab, pertuzumab, ranibizumab, reslizumab, rituximab, teplizumab, tocilizumab/atlizumab, tositumomab, trastuzumab, Proxinium™, Rencarex™, ustekinumab, and zalutumumab.

"TIMP1" or TIMP-1 refers to Tissue inhibitors of metalloproteases type 1 endogenously derived from the host cell, such as Chinese Hamster TIMP-1 of a CHO cell.

"LGALS3BP" refers to lectin, galactoside-binding soluble 3 binding protein endogenously derived from the host cell, such as Chinese Hamster LGALS3BP of a CHO cell.

NID1 or NID1-1 as used herein refers to Nidogen 1. On the CHO K1 reference genome this gene exists in 2 isoforms, hence the NID1-1 and NID1-2.

"BGN" refers to gene of biglycan.

"CTSD" refers to a Cathepsin D protein endogenously derived from the host cell, such as Chinese Hamster CTSD of a CHO cell.

Timp1 Identifiers from NCBI:
Gene ID: 100770193; mRNA: XM_007630118.1, XM_007630119.1, JP061669.1, JI873443.1
Protein: XP_003512290.1, XP_007628308.1, XP_007628309.1, EGW14768.1, ERE65804.1
LGALS3BP Identifiers from NCBI:
Gene ID: 100767541; mRNA: XM_003498817.2, XM_007622088.1
Protein: XP_007620278.1, XP_003498865.1, EGV97878.1
NID1 Identifiers from NCBI:
Gene ID: 100766031; mRNA: XM_003509885.2, XM_003507587.2, XM_007632645.1, KE673075.1
Proteins: ERE78436.1, XP_007630835.1, XP_003507635.2, XP_003509933.2
BGN Identifiers from NCBI:
Gene ID: 100771022; mRNA: XM_003506540.2, XM_007628144.1, KE685970.1:158610-162415 (+), JH000676.1:731964-735640 (−)
Protein: XP_003506588.1, XP_007626334.1, ERE63792.1, EGV92105.1
CTSD Identifiers from NCBI:
Gene ID: 100766628; mRNA, XM_003510234.2, XM_007611606.1, JI884212.1, JP051918.1, 3H001272.1: 176080-187386 (−), KE672442.1:201083-212389 (+)
Protein, EGW04839.1, ERE79325.1, XP_007609796.1, XP_003510282.1

Specific Embodiments of the Invention

The present invention relates to a CHO cell modified to disrupt expression of one or more endogenous proteins selected from the group consisting of TIMP1, NID1-1, NID1-2, BGN, and LGALS3BP.

In some embodiments the CHO cell is modified to disrupt expression of TIMP1.

In some embodiments the CHO cell is modified to disrupt expression of LGALS3BP.

In some embodiments the CHO cell is modified to disrupt expression of NID1-1, NID1-2, or both.

In some embodiments the CHO cell is modified to disrupt expression of CTSD.

In some embodiments the CHO cell is modified to disrupt expression of BGN.

In some embodiments the CHO cell is modified to disrupt expression of the endogenous proteins TIMP1, NID1-1, NID1-2, BGN, and LGALS3BP.

In some embodiments the CHO cell is modified to disrupt expression of
(a) at least 5 endogenous proteins;
(b) at most 50 endogenous proteins; or
(c) between 5 and 50 endogenous proteins.

In some embodiments the CHO cell is modified to disrupt expression of TIMP1, LGALS3BP, NID1-1, NID1-2, BGN and CTSD.

In some embodiments the expression of at least one endogenous protein is disrupted by knockdown of the gene encoding the endogenous protein.

In some embodiments the expression of at least one endogenous protein is disrupted by knockout of the gene encoding the endogenous protein.

In some embodiments the CHO cell of the invention comprises a nucleic acid sequence encoding a recombinant protein of interest, the nucleic acid sequence being extrachromosomal or chromosomally integrated and under the control of an inducible or constitutive promoter.

In some embodiments the cell of the invention produce higher levels of said recombinant protein of interest and/or has an increased cell-density as compared to a relevant control cell without disrupted expression of one or more endogenous proteins, such as a wild type CHO cell.

In some embodiments the eukaryotic host cell used according to the invention is a CHO cell, optionally selected from a CHO-K1, CHO-S and CHO DG44 cells.

According to the cells and methods invention, the gene expression of certain genes are "disrupted" by at least one step selected from the group consisting of gene silencing, gene knock-down, gene knock-out, delivery of a dominant negative construct, conditional gene knock-out, and/or by gene alteration with respect to a specific gene.

The term "gene expression", as used herein, is meant to encompass at least one step selected from the group consisting of DNA transcription into mRNA, mRNA processing, non-coding mRNA maturation, mRNA export, translation, protein folding and/or protein transport.

The inhibition or reduction of gene expression of a gene refers to methods which directly interfere with gene expression, encompassing, but not restricted to, inhibition or reduction of DNA transcription, e.g., by use of specific promoter-related repressors, by site specific mutagenesis of a given promoter, by promoter exchange, or inhibition or reduction of translation, e.g., by RNAi induced post-transcriptional gene silencing. The expression of a dysfunctional, or inactive gene product with reduced activity, can, for example, be achieved by site specific or random mutagenesis, insertions or deletions within the coding gene.

The inhibition or reduction of the activity of gene product can, for example, be achieved by administration of, or incubation with, an inhibitor to the respective enzyme, prior to or simultaneously with protein expression. Examples for such inhibitors include, but are not limited to, an inhibitory peptide, an antibody, an aptamer, a fusion protein or an antibody mimetic against said enzyme, or a ligand or receptor thereof, or an inhibitory peptide or nucleic acid, or a small molecule with similar binding activity.

Other ways to inhibit the enzyme are the reduction of specific cofactors of the enzyme in the medium, like copper, which is a PAM specific ion cofactor (e.g., in the form of CuS04), ascorbate, which acts as an electron donor for PAM, molecular oxygen, catalase and others known today to the skilled artisan, or yet to be discovered in the future.

Gene silencing, gene knock-down and gene knock-out refers to techniques by which the expression of a gene is reduced, either through genetic modification or by treatment with an oligonucleotide with a sequence complementary to either an mRNA transcript or a gene. If genetic modification of DNA is done, the result is a knock-down or knock-out organism. If the change in gene expression is caused by an oligonucleotide binding to an mRNA or temporarily binding to a gene, this results in a temporary change in gene expression without modification of the chromosomal DNA and is referred to as a transient knock-down.

In a transient knock-down, which is also encompassed by the above term, the binding of this oligonucleotide to the active gene or its transcripts causes decreased expression through blocking of transcription (in the case of gene-binding), degradation of the mRNA transcript (e.g. by small interfering RNA (siRNA) or RNase-H dependent antisense) or blocking either mRNA translation, pre-mRNA splicing sites or nuclease cleavage sites used for maturation of other functional RNAs such as miRNA (e.g., by Morpholino oligos or other RNase-H independent antisense). Other approaches involve the use of shRNA (small hairpin RNA, which is a sequence of RNA that makes a tight hairpin turn that can be used to silence gene expression via RNA interference), esiRNA (Endoribonuclease-prepared siRNAs, which are a mixture of siRNA oligos resulting from cleavage of long double-stranded RNA (dsRNA) with an endoribonuclease), or the activation of the RNA-induced silencing complex (RISC).

Other approaches to carry out gene silencing, knock-down or knock-out are known to the skilled person from the respective literature, and their application in the context of the present invention is considered as routine.

Gene knock-out refers to techniques by which the expression of a gene is fully blocked, i.e. the respective gene is inoperative, or even removed. Methodological approaches to achieve this goal are manifold and known to the skilled person. Examples are the production of a mutant which is dominantly negative for the given gene. Such mutant can be produced by site directed mutagenesis (e.g., deletion, partial deletion, insertion or nucleic acid substitution), by use of suitable transposons, or by other approaches which are known to the skilled person from the respective literature, the application of which in the context of the present invention is thus considered as routine. One example for a newly developed technique which the skilled person would consider as useful in the context of the present invention is knock-out by use of targeted Zinc Finger Nucleases. A respective Kit is provided by Sigma Aldrich as "CompoZR knockout ZFN". Another approach encompasses the use of Transcription activator-like effector nucleases (TALENs).

The delivery of a dominant negative construct involves the introduction of a sequence coding for a dysfunctional enzyme, e.g., by transfection. Said coding sequence is functionally coupled to a strong promoter, in such way that the gene expression of the dysfunctional enzyme overrules the natural expression of the wild type enzyme, which, in turn, leads to an effective physiological defect of the respective enzyme activity.

A conditional gene knock-out allows to block gene expression in a tissue- or time-specific manner. This is done, for example, by introducing short sequences called loxP sites around the gene of interest. Again, other approaches are known to the skilled person from the respective literature, and their application in the context of the present invention is considered as routine.

One other approach is gene alteration which may lead to a dysfunctional gene product or to a gene product with reduced activity. This approach involves the introduction of frame shift mutations, nonsense mutations (i.e., introduction of a premature stop codon) or mutations which lead to an amino acid substitution which renders the whole gene product dysfunctional, or causing a reduced activity. Such gene alteration can for example be produced by mutagenesis (e.g., deletion, partial deletion, insertion or nucleic acid substitution), either unspecific (random) mutagenesis or site directed mutagenesis.

Protocols describing the practical application of gene silencing, gene knock-down, gene knock-out, delivery of a dominant negative construct, conditional gene knock-out, and/or gene alteration are commonly available to the skilled artisan, and are within his routine. The technical teaching provided herein is thus entirely enabled with respect to all conceivable methods leading to an inhibition or reduction of gene expression of a gene product, or to the expression of a dysfunctional, or inactive gene product, or with reduced activity.

Preparation of Protein of Interest

The invention also relates to a method of preparing a protein of interest as mentioned above. The protein of interest described herein may be produced by means of recombinant nucleic acid techniques. In general, a cloned nucleic acid sequence is modified to encode the desired protein. This modified sequence is then inserted into an expression vector, which is in turn transformed or transfected into host cells. Higher eukaryotic cells, in particular cultured mammalian cells, are preferred as host cells. The complete nucleotide and amino acid sequences for human Optional amino acid sequence alterations may be accomplished by a variety of techniques. Modification of the nucleic acid sequence may be by site-specific mutagenesis. Techniques for site-specific mutagenesis are well known in the art and are described in, for example, Zoller and Smith (DNA 3: 479-488, 1984) or "Splicing by extension overlap", Horton et al., Gene 77, 1989, pp. 61-68. Thus, using the nucleotide and amino acid sequences of the protein of interest, one may introduce the alteration (s) of choice. Likewise, procedures for preparing a DNA construct using polymerase chain reaction using specific primers are well known to persons skilled in the art (cf. PCR Protocols, 1990, Academic Press, San Diego, Calif., USA).

The nucleic acid construct encoding the protein of interest may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., Molecular Cloning: A Laboratory Manual, 2nd. Ed. Cold Spring Harbor Laboratory, Cold Spring Harbor, N.Y., 1989).

The nucleic acid construct encoding the protein of interest may also be prepared synthetically by established standard methods, e. g. the phosphoamidite method described by Beaucage and Caruthers, Tetrahedron Letters 22 (1981), 1859-1869, or the method described by Matthes et al., EMBO Journal 3 (1984), 801-805. According to the phosphoamidite method, oligonucleotides are synthesised, e. g. in an automatic DNA synthesiser, purified, annealed, ligated and cloned in suitable vectors. The protein of interest may also be prepared by polymerase chain reaction using specific primers, for instance as described in U.S. Pat. No. 4,683, 202, Saiki et al., Science 239 (1988), 487-491, or Sambrook et al., supra.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct is preferably a DNA construct. DNA sequences for use in producing the protein of interest will typically encode a pre-pro polypeptide at the amino-terminus of the protein of interest to obtain proper post-translational processing (e. g. gamma-carboxylation of glutamic acid residues) and secretion from the host cell.

The DNA sequences encoding the protein of interest are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i. e. a vector, which exists as an extrachromosomal entity, the replication of which is independent of chromosomal replication, e. g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the protein of interest is operably linked to additional segments required for transcription of the DNA. In general, the expression vector is derived from plasmid or viral DNA, or may contain elements of both. The term "operably linked" indicates that the segments are arranged so that they function in concert for their intended purposes, e. g. transcription initiates in a promoter and proceeds through the DNA sequence coding for the polypeptide.

Expression vectors for use in expressing a protein of interest will comprise a promoter capable of directing the transcription of a cloned gene or cDNA. The promoter may be any DNA sequence, which shows transcriptional activity in the host cell of choice and may be derived from genes encoding proteins either homologous or heterologous to the host cell.

Examples of suitable promoters for directing the transcription of the DNA encoding a protein of interest in mammalian cells are the SV40 promoter (Subramani et al., Mol. Cell Biol. 1 (1981), 854-864), the MT-1 (metallothionein gene) promoter (Palmiter et al., Science 222 (1983), 809-814), the CMV promoter (Boshart et al., Cell 41: 521-530, 1985) or the adenovirus 2 major late promoter (Kaufman and Sharp, Mol. Cell. Biol, 2: 1304-1319, 1982).

The DNA sequences encoding the protein of interest may also, if necessary, be operably connected to a suitable terminator, such as the human growth hormone terminator (Palmiter et al., Science 222, 1983, pp. 809-814) or the TPI 1 (Alber and Kawasaki, J. Mol. Appl. Gen. 1, 1982, pp. 419-434) or ADH3 (McKnight et al., The EMBO J. 4, 1985, pp. 2093-2099) terminators. Expression vectors may also contain a set of RNA splice sites located downstream from the promoter and upstream from the insertion site for the sequence itself encoding the protein of interest. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. Nucl. Acids Res. 9: 3719-3730, 1981) or the polyadenylation signal from the gene encoding the protein of interest. The expression vectors may also include a noncoding viral leader sequence, such as the adenovirus 2 tripartite leader, located between the promoter and the RNA splice sites; and enhancer sequences, such as the SV40 enhancer.

To direct the protein of interest into the secretory pathway of the host cells, a secretory signal sequence (also known as a leader sequence, prepro sequence or pre sequence) may be provided in the recombinant vector. The secretory signal sequence is joined to the DNA sequences encoding the protein of interest in the correct reading frame. Secretory signal sequences are commonly positioned 5' to the DNA sequence encoding the peptide. The secretory signal sequence may be that, normally associated with the protein or may be from a gene encoding another secreted protein.

The procedures used to ligate the DNA sequences coding for the protein of interest, the promoter and optionally the terminator and/or secretory signal sequence, respectively, and to insert them into suitable vectors containing the information necessary for replication, are well known to persons skilled in the art (cf., for instance, Sambrook et al., Molecular Cloning: A Laboratory Manual, Cold Spring Harbor, N.Y., 1989).

Methods of transfecting mammalian cells and expressing DNA sequences introduced in the cells are described in e. g. Kaufman and Sharp, J. Mol. Biol. 159 (1982), 601-621; Southern and Berg, J. Mol. Appl. Genet. 1 (1982), 327-341; Loyter et al., Proc. Natl. Acad. Sci. USA 79 (1982), 422-426; Wigler et al., Cell 14 (1978), 725; Corsaro and Pearson, Somatic CellGenetics 7 (1981), 603, Graham and van der Eb, Virology 52 (1973), 456; and Neumann et al., EMBO J. 1 (1982), 841-845. Cloned DNA sequences are introduced into cultured mammalian cells by, for example, calcium phosphate-mediated transfection (Wigler et al., Cell 14: 725-732, 1978; Corsaro and Pearson, Somatic Cell Genetics 7: 603-616, 1981; Graham and Van der Eb, Virology 52d: 456-467, 1973) or electroporation (Neumann et al., EMBO J. 1: 841-845, 1982).

To identify and select cells that express the exogenous DNA, a gene that confers a selectable phenotype (a selectable marker) is generally introduced into cells along with the gene or cDNA of interest. Preferred selectable markers include genes that confer resistance to drugs such as neomycin, hygromycin, and methotrexate. The selectable marker may be an amplifiable selectable marker. A preferred amplifiable selectable marker is a dihydrofolate reductase (DHFR) sequence. Selectable markers are reviewed by Thilly (Mammalian Cell Technology, Butterworth Publishers, Stoneham, Mass., incorporated herein by reference). The person skilled in the art will easily be able to choose suitable selectable markers.

Selectable markers may be introduced into the cell on a separate plasmid at the same time as the gene of interest, or they may be introduced on the same plasmid. If, on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically 1-2 days, to begin expressing the gene of interest. As used herein the term "appropriate growth medium" means a medium containing nutrients and other components required for the growth of cells and the expression of the human Protein of interest of interest. Media generally include a carbon source, a nitrogen source, essential amino acids, essential sugars, vitamins, salts, phospholipids, protein and growth factors. For production of gamma-carboxylated proteins, the medium will contain vitamin K, preferably at a concentration of about 0.1 Ilg/ml to about 5 Lg/ml. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby increasing expression levels. Clones of stably transfected cells are then screened for expression of the protein of interest.

The host cell into which the DNA sequence encoding the protein of interest is introduced may be any cell, such as one which is capable of producing the posttranslational modified proteins, such as higher eukaryotic cells.

Example 1

Identification of the Top-6 Secreted Proteins in Our CHO Cell Line

First protein mass spectroscopy data of the extracellular media from several CHO cell cultures was analyzed by a series of processes implemented and executed in python (www.python.org/):

Relevant data was extracted from mass spec software data output files, e.g. short and long identifiers, top 3 matched peptide intensity sums and identifiers for potential homologs.

Homologs were collapsed by sum and intensity sums were normalized by converting into percentage of total peptide intensity sums.

External information about run conditions was added to the data.

Top 20 proteins were then selected based on the criteria that they were present in at least half of our samples and have the 20 highest median normalized intensity sum values.

These 20 proteins were then further analyzed by gene ontology to exclude proteins for various reasons:

Gene ontology, as compiled by e.g. the Gene Ontology Consortium (GO, geneontology.org/), can be used to infer the origin of gene products. The means by which proteins reach the media of a cell culture may be by e.g. controlled secretion or cell lysis. We were primarily interested in proteins that had reached the media by secretion, and specifically not interested in proteins that had reached in by cell lysis. If, by gene ontology, we saw that a protein mainly resides intracellularly, we assumed that its presence in the media was not due to organized secretion, but rather cell lysis and consequently knock down or knock out is unlikely to free up secretory capacity.

We assigned gene ontology terms to our top 20 proteins by using the GO Cross-species Homology database (GO CHO, ebdrup.biosustain.dtu.dk/gocho/) which extracts terms for a gene product by looking for similarly named gene product in a selection of related organisms under the assumption that gene function, and thus GO terms, are largely conserved between closely related species.

Using the GO CHO interface, we then exclude proteins from the top 20 list that are not known to be present in the extracellular media Known from the GeneOntology database. This is a database of manual (literature) and electronic (literature and various methods) annotation for gene products.

Additionally we excluded proteins form the top 20 list, that are known to be essential or important for the functioning of the cell.

These processes ultimately resulted in the identification of 6 secreted proteins. (TIMP1, BGN, CTSD; NID1-1, NID1-2 and LGALS3BP).

The selected gRNA was synthesised as synthetic oligoes, annealed to make dsDNA, and cloned into an expression vector using USER cloning (New England Biolabs) according to the manufacturer's protocol.

First all 6 genes were knocked out individually in CHO-S cells. Thereafter 5 genes were knocked out in the knock out cell line that already contained TIMP1 to create a cell lines that contained disrupted coding sequences for all 6 genes.

The annealed oligo's were cloned into expression vectors using USER cloning, according to the manufacturers (New England Biolabs) protocol.

The plasmids with the cloned gRNA oligo's were midiprepped and transfected with a GFP labeled Cas9 encoding plasmid (Ronda C, Pedersen L E, et al Biotechnol Bioeng. 2014 August; 111(8):1604-16. & Grav L M, et al, Biotechnol J. 2015 September; 10(9):1446-56.) into CHO-S cells from Thermo, grown in CD-CHO media with 8 mM Glutamine, using FreeStyle transfection agent (Thermo) according to the manufacturers recommendations.

Example 2

Preparation of CHO KO Cells

The sgRNA expression constructs were designed by fusing tracrRNA and crRNA into a chimeric sgRNA (Jinek et al., 2012) and located immediately downstream of a U6 promoter (Chang et al., 2013). Initially, the sgRNA expression cassette was synthesized as a gBlock (Integrated DNA Technologies) and subcloned into the pRSFDuet-1 vector (Novagen, Merck) using KpnI and HindIII restriction sites. This pRSFDuet-1/sgRNA expression vector was used as backbone in a PCR-based uracil specific excision reagent (USER) cloning method. This method was designed to easily and rapidly change the 19 bp-long variable region (N19) of the sgRNA in order to generate our sgRNA constructs. From the pRSFDuet-1/sgRNA expression vector, a 4221 bp-long amplicon (expression vector backbone) was generated by PCR (1×: 98'C for 2 min; 30×: 98'C for 10 s, 57'C for 30 s, 72'C for 4 min 12 s; 1×: 72'C for 5 min) using two uracil-containing primers (sgRNA Backbone fw and sgRNA Backbone rv, Integrated DNA Technologies, Table 2) and the X7 DNA polymerase. Subsequent to Fastdigest DpnI (Thermo Fisher Scientific) treatment, the amplicon was purified from a 2% agarose TBE gel using the QIAEX II Gel Extraction Kit (Qiagen). In parallel, 54 bp-long and 53 bp-long single stranded oligos, (sense and antisense strand, respectively) comprising the variable region of the sgRNA, were synthesized (TAG Copenhagen, Table 2). Annealing of the sense and antisense single stranded oligos (100 pM) were done with slow cooling from 95° C. to 25° C. over 15 min in a thermocycler in buffer 4 from New England Biolabs. The annealed oligos were then mixed with the gel purified expression vector backbone and treated with USER enzyme (New England Biolabs) according to manufacturer's recommendations. After USER enzyme treatment, the reaction mixture was transformed into *E. coli* Mach1 competent cells (Life Technologies) according to standard procedures. Transformant clones were selected on 50 pg/mL Kanamycin (Sigma-Aldrich) LB plates. All constructs were verified by sequencing and purified by NucleoBond Xtra Midi EF (Macherey-Nagel) according to manufacturer's guidelines.

The CHO codon optimized Cas9 expression vector applied in the study is described in (Ronda C, Pedersen L E, et al Biotechnol Bioeng. 2014 August; 111(8):1604-16. & Gray L M, et al, Biotechnol J. 2015 September; 10(9):1446-56.). The CRISPy bioinformatic tool (staff.biosustain.dtu.dk/ilaeb/crisDv/) was applied for generating sgRNAs targeting the 6 genes chosen for KO. The sgRNA targeting the 6 genes are described in table 1.

TABLE 1

| ID | Oligo names and sequences. Seq (5'-3') |
|---|---|
| gRNA_BGN_1140221_fwd (SEQ ID NO: 1) | GGAAAGGACGAAACACCGCGGTCAGTGACGCAGCGGAGTTTTAGAGCTAGAAAT |
| gRNA_TIMP1_1673356_fwd (SEQ ID NO: 2) | GGAAAGGACGAAACACCGCCTTCTGCAACTCCGACCTGTTTTAGAGCTAGAAAT |
| gRNA_CTSD_1486038_fwd (SEQ ID NO: 3) | GGAAAGGACGAAACACCGCAAGTTCACGTCTATCCGTGTTTTAGAGCTAGAAAT |
| gRNA_LGALS3BP_390023_fwd (SEQ ID NO: 4) | GGAAAGGACGAAACACCGATCTCCACGCGGCCCTCACGTTTTAGAGCTAGAAAT |
| gRNA_NID1-rna13382_1237189_fwd (SEQ ID NO: 5) | GGAAAGGACGAAACACCGTGACTGAGCCTGATCCGGAGTTTTAGAGCTAGAAAT |
| gRNA_NID1-rna15820_1455331_fwd (SEQ ID NO: 6) | GGAAAGGACGAAACACCGTTGCGGCCGAGATGGTCAAGTTTTAGAGCTAGAAAT |
| gRNA_BGN_1140221_rev (SEQ ID NO: 7) | CTAAAACTCCGCTGCGTCACTGACCGCGGTGTTTCGTCCTTTCCACAAGATAT |
| gRNA_TIMP1_1673356_rev (SEQ ID NO: 8) | CTAAAACAGGTCGGAGTTGCAGAAGGCGGTGTTTCGTCCTTTCCACAAGATAT |
| gRNA_CTSD_1486038_rev (SEQ ID NO: 9) | CTAAAACACGGATAGACGTGAACTTGCGGTGTTTCGTCCTTTCCACAAGATAT |
| gRNA_LGALS3BP_390023_rev (SEQ ID NO: 10) | CTAAAACGTGAGGGCCGCGTGGAGATCGGTGTTTCGTCCTTTCCACAAGATAT |
| gRNA_NID1-rna13382_1237189_rev (SEQ ID NO: 11) | CTAAAACTCCGGATCAGGCTCAGTCACGGTGTTTCGTCCTTTCCACAAGATAT |
| gRNA_NID1-rna15820_1455331_rev (SEQ ID NO: 12) | CTAAAACTTGACCATCTCGGCCGCAACGGTGTTTCGTCCTTTCCACAAGATAT |
| MiSeq_BGN_1140221_fwd (SEQ ID NO: 13) | CATGGTGGCTACTACTGCTTTT |
| MiSeq_TIMP1_1673356_fwd (SEQ ID NO: 14) | TCACTGATAACCTCCAGCAAGG |
| MiSeq_CTSD_1486038_fwd (SEQ ID NO: 15) | CTCAGCAGGTGACTGATTGGAG |
| MiSeq_LGALS3BP_390023_fwd (SEQ ID NO: 16) | GCACAAAGCATCGAAGTCCTG |
| MiSeq_NID1-rna13382_1237189_fwd (SEQ ID NO: 17) | TGGGTAGGGACTGCTACCG |
| MiSeq_NID1-rna15820_1455331_fwd (SEQ ID NO: 18) | TGCCATCCATTCTTGCAACTTC |
| MiSeq_BGN_1140221_rev (SEQ ID NO: 19) | CAAGGTGGGCATCAACGACT |
| MiSeq_TIMP1_1673356_rev (SEQ ID NO: 20) | ATGGCCAAAGTGGATCTATGCAA |
| MiSeq_CTSD_1486038_rev (SEQ ID NO: 21) | AGCCTGGAGTATCCTTGGGTAG |
| MiSeq_LGALS3BP_390023_rev (SEQ ID NO: 22) | GCATCTAAAATGTTCCAGAGGTTGT |

TABLE 1-continued

| ID | Oligo names and sequences. Seq (5'-3') |
|---|---|
| MiSeq_NID1-rna13382_1237189_rev (SEQ ID NO: 23) | TGGAGTCATCATGGACACACTC |
| MiSeq_NID1-rna15820_1455331_rev (SEQ ID NO: 24) | TCCCATTTGGTTTCTCAAGGTTT |

CHO cells e.g. CHO-S cells from Life Technologies were grown in appropriate medium e.g. CD CHO medium (Life Technologies) supplemented with 8 mM L-Glutamine and cultivated in shake flasks. The cells were incubated at 37° C., 5% CO2, with 120 rpm shaking and passaged every 2-3 days. Transfection was performed with the expression vectors encoding CHO optimized Cas9 and sgRNA targeting the respective KO sites, described above. For each sample, $3 \times 10^6$ cells were transfected with a total of 3.75 pg of DNA. 16 hours post transfection, the samples were incubated at 30° C. for 32 hours before transferred back to 37° C. The transfected cells were single cell sorted into 96 well plates, using Fluorescence-activated cell sorting (FACS) to harvest GFP positive cells and cultivated at 37° C., 5% CO2 for 3 weeks. Drying out of the wells was avoided by topping up with fresh media as needed. Growing clones were collapsed into single 96 well plates and a sample pr growing clone was taken out for genomic analysis to identify gene KO's. Genomic DNA is prepared using Quick Extract kit (Epicentre) according to the manufacturers recommendations. Amplicons covering the targeted sites were made using target specific miSeg primers (tableX) using Phusion polymerase in a thermocycler using the following programme: 1×: 95° C. for 7 min; 20×: 95° C. for 45 s, 69.5° C. for 30 s (Δ−0.5° C./cycle), 72° C. for 30s; 1×: 72° C. for 7 min The resulting amplicons are purified using AMPure XP Beads (Beckman Coulter) according to the manufacturers recommendations.

The purified amplicons are indexed using the Nextera XT indexing kit from Illumina using the following protocol:

| Mix | x1 |
|---|---|
| DNA | 5.0 µL |
| Nextera XT Index 1 | 2.5 µL |
| Nextera XT Index 2 | 2.5 µL |
| 2x KAPA HiFI HotStart Ready Mix | 12.5 µL |
| H2O | 2.5 µL |
| | 25 µl | and run on a thermal cycler using the following program: 1×: 95° C. for 3 min; 8×: 95° C. for 30 sec, 55° C. for 30 sec 72° C. for 30 sec; 1×: 72° C. for 5 min The resulting indexed libraries are purified using AMPure XP Beads (Beckman Coulter) according to the manufacturers recommendations.

The libraries are normalized to 10 nM, pooled and run on an miSeq DNA sequencer (Illumina) using the following protocol:

Bring 10 nM Library to 4 nM by combining:
4 µl of 10 nM library
6 µl Hybridisation buffer1 (HT1) (Illumina)

Combine together:
5 µl of 4 nM library
5 µl of 0.2N NaOH
Vortex briefly and spin 1 minute at 280 g.
Incubate for 5 minutes at room temperature for denaturing DNA into single strands.
Add 990 µl pre-chilled HT1 (library is now 20 pM & denatured in 1 mM NaOH).
Kept on ice from now on.
The denatured libraries are diluted to 10 pM with pre-chilled HT1 and spiked with 30 µl denatured Illumina PhiX Control (Illumina), immediately loaded on a miSeg cartridge and run on a Illumina miSeq Desktop sequencer.

After MiSeq the sequence data are analyzed by running them through a series of steps executed using python. First paired sequences are merged into one sequence. Then sequences are quality checked and trimmed or discarded if below threshold. Sequences are then aligned to wild type version of the target sites. Each clone is then identified on the basis of its unique index pair and analyzed in regard to the genomic situation at each of the target sites. If it is clear that all target sites have been disrupted in a manner that results in a frameshift and the data is generally plausible and clean, the clone is saved for further propagation.

The KO's were all generated as single KO's first, and thereafter the TIMP1 KO was used as basis for the KO of the other 5 gene targets in one single procedure, where all 5 gRNA vectors were co-transfected with the Cas9 vector, to generate a CHO Cell line with all 6 genes knocked out (6×SecKO), using the protocols described above.

Example 3

Characterization of CHO KO Cells

The CHO cells were analyzed for growth and rituximab expression using the following protocol:
Thaw cell from Cell Bank
Maintain and propagate cells for 3 passages
On Day 1: Wash cells and culture o/n without anti-clumping agent
On Day 2: Count cells and adjust to 1,000,000 cells/mL (3×125 mL shake flasks with 30 mL for each cell line), transfect cells with Rituximab expression vector according to protocol described above
On day 3, Take out a 1 mL sample from each flask for cell count and determination of transfection efficiency and replace with 1 mL fresh medium (containing 60 uL Anti-clumping agent per mL)
On day 4 Take out a 1 mL sample from each flask for cell count and determination of transfection efficiency and replace with 1 mL fresh medium
On day 5: Take out a 1 mL sample from each flask for cell count and determination of transfection efficiency and replace with 1 mL fresh medium, and harvest supernatants for analysis of Rituximab titer.

All incubations are done at 37° C., 5% CO2 120 rpm in a Multitron Incubator (Inforss).

Rituximab titers were determined using the Octet RED96 system from Pall according to the manufacturer's recommendations for detection of IgG.

Cells were counted using a Nucleocounter NC-200 from Chemometec according to the manufacturers recommendations for counting CHO cells From FIG. 1 is seen a positive effect of knocking out all genes except maybe for BGN.

Figure 2:
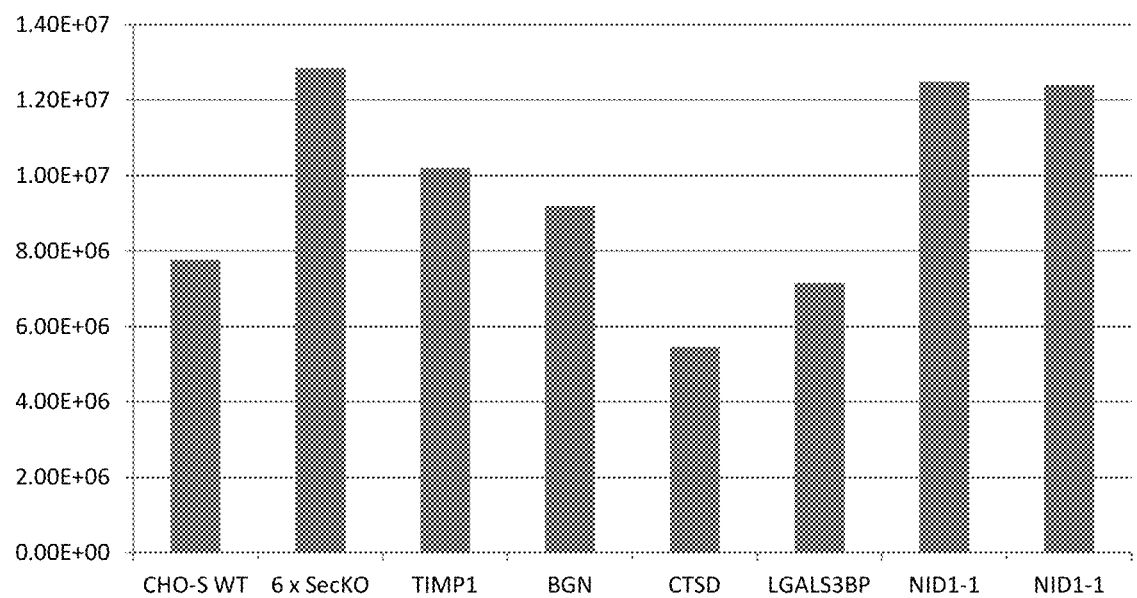
FIG. 2: Maximum Cell Density of a multiplex secretory KO and individual secretory KO clones (normalized to CHO-S WT. Maximum reached cell density in shakeflasks, for the 6SecKO and for Cell lines with the genes knocked out individually, compared to wt.

From FIG. 2 is seen that the 6×SecKO reach significantly higher maximal cell densities than the wt CHO-S cells. The gene KO that seems to be the major contributor to this phenotype is the knocking out of the NID1-1 genes.

Example 4

Quantification of the Host Cell Protein (HCP) Content in the Supernatant

Used media from CHO-S, 6×secKO and 11×secKO, was harvested and the HCP were TCA precipitated using the following protocol:
1. Add 1 volume of TCA stock to 4 volumes of protein sample. (250 ul TCA+1000 ul SN) i.e. in 1.5 ml tube with maximum vol., add 250 µl TCA to 1.0 ml sample.
2. Incubate 10 min at 4° C.
3. Spin tube in microcentrifuge at 14K rpm, 5 min.
4. Remove supernatant, leaving protein pellet intact. Pellet should be formed from whitish, fluffy ppt.
5. Wash pellet with 200l cold acetone.
6. Spin tune in microfuge at 14K rpm, 5 min.
7. Repeat steps 4-6 for a total of 2 acetone washes.
8. Dry pellet by placing tube in 95° C. heat block for 5-10 min to drive off acetone.
9. Dissolve the pellets in 200 ul 1% SDS, 50 mM TRIS, pH 7.5 at 95 C The protein content of the redissolved HCP was determined using Bradford Protein assay (Pierce) according to the suppliers instructions, and using absorption at 280 nm on a nanodrop (Thermo Fischer). The presence of HCP was also determined using an antibody based CHO cell HCP kit (FortéBIO).

Figure 3:
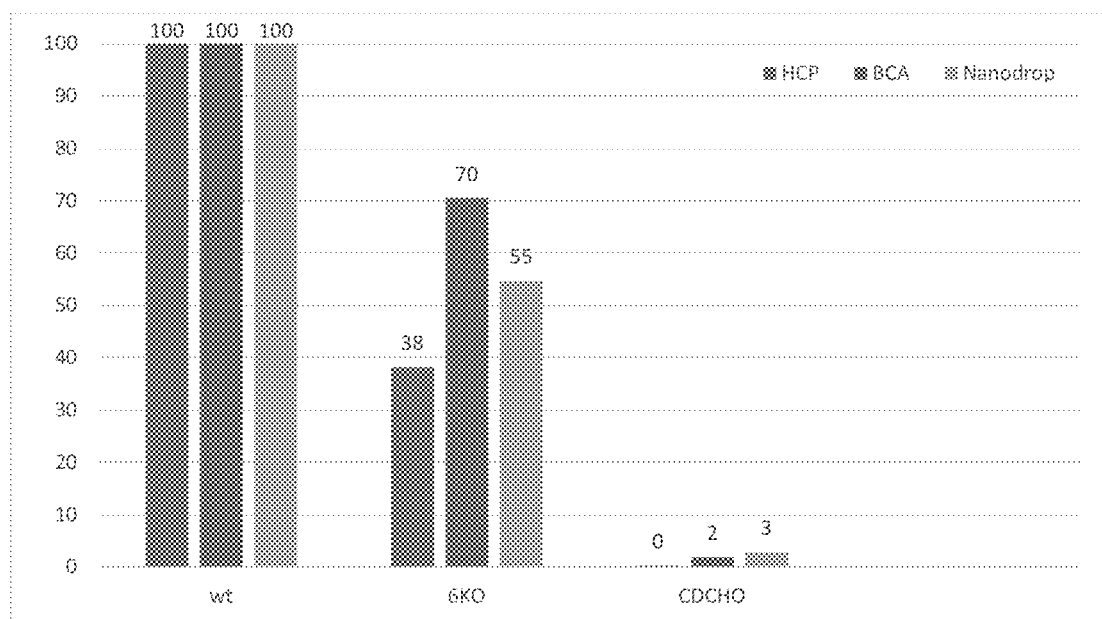
FIG. 3: Presence of Host Cell Proteins (HCP) (normalised to wt CHO-S) in used media measured by quantity (BCA and Nanodrop) and immunogenicity (HCP). CDCHO is HCP free CHO media.

Analysis of the HCP present in the used media shows that the 2 KO's contain significantly lower amounts of HCP in the used media that the CHO-S cell line (between approx 55% and 70% compared to CHO-S,) and even less immunogenic HCP (approx 35%), shown by the antibody based HCP assay. (See FIG. 3).

Figure 4:
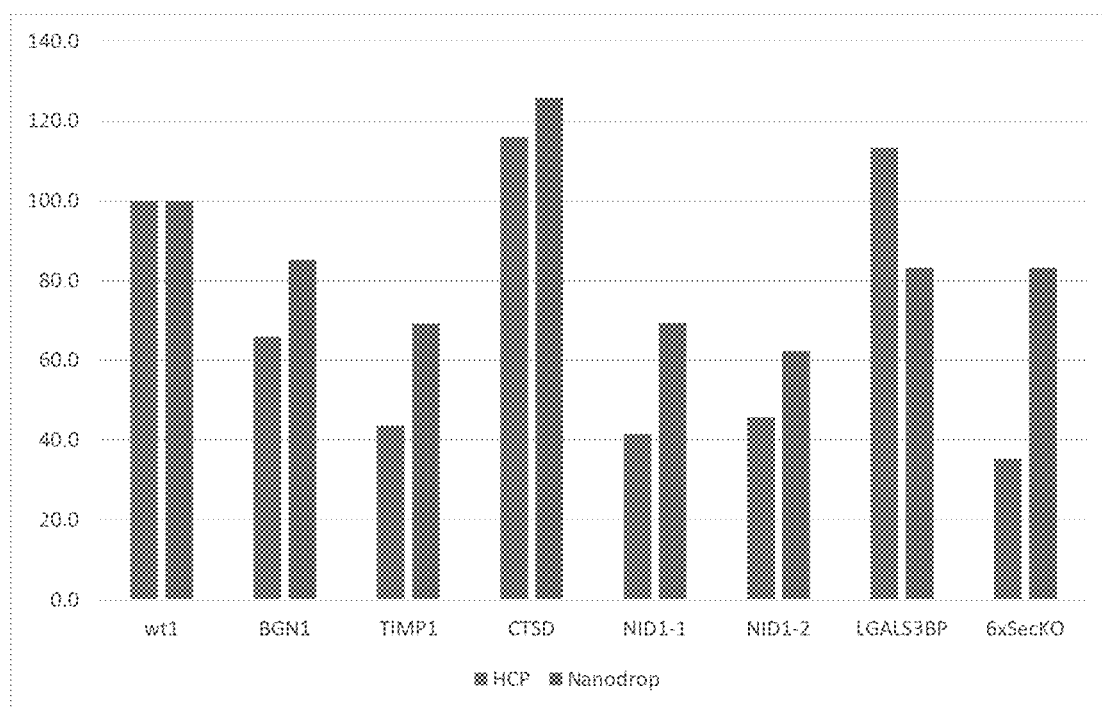
FIG. 4: Analysis of the HCP present in used media from cells with the genes TIMP1, BGN, NID1-1 and NID1-2 knocked out individually. Numbers are normalized to wt being 100.

Analysis of the HCP present in used media from cells with the genes knocked out individually, shows that especially TIMP1, BGN, NID1-1 and NID1-2 removal reduces the immunogenic signal seen in the antibodybased assay (see FIG. 4)

LIST OF REFERENCES

WO 2007/006808 A1
WO 2012/082509 A2
Baycin-Hizal et al., J Proteome Res 2012; 11(11):5265-5276
Chaudhuri et al., J Bioprocess Biotech 2015; 5:7
Datta et al., Biotechnol Bioeng 2013; 110(5):1255-1271
Kim et al., Appl Microbiol Biotechnol 2012; 93:917-930
Slade et al., J Proteome Res 2012; 11:6175-6186
Zhang, "Mammalian Cell Culture for Biopharmaceutical production", In: Manual of Industrial Microbiology and Biotechnology, Edition: 3rd ed., Chapter: 12, Publisher: ASM Press, Washington, D.C., pp. 157-178 (2010)
Lee et al., Biotechnology Journal 2015; 10(7):979-994
Walsh, Nat Biotechnol 2014; 32:992-1000.

The invention claimed is:

1. A Chinese hamster ovary (CHO) cell modified to disrupt expression of one or more endogenous proteins selected from the group consisting of Tissue inhibitors of metalloproteases type 1 (TIMP1), Nidogen 1 isoform 1 (NID1-1), Nidogen 1 isoform 2 (NID1-2), Biglycan (BGN), and Lectin, galactoside-binding soluble 3 binding protein (LGALS3BP).

2. The CHO cell of claim 1, wherein the CHO cell is modified to disrupt expression of TIMP1.

3. The CHO cell of claim 1, wherein the CHO cells is modified to disrupt expression of LGALS3BP.

4. The CHO cell of claim 1, wherein the CHO cell is modified to disrupt expression of NID1-1, NID1-2, or both.

5. The CHO cell of claim 1, wherein the CHO cell is modified to disrupt expression of TIMP1, LGALS3BP, NID1-1, NID1-2, BGN, and Cathepsin D (CTSD).

6. The CHO cell of claim 1, wherein the expression of at least one endogenous protein is disrupted by knockdown of the gene encoding the endogenous protein.

7. The CHO cell of claim 1, wherein the expression of at least one endogenous protein is disrupted by knockout of the gene encoding the endogenous protein.

8. The CHO cell of claim 1, which comprises a nucleic acid sequence encoding a recombinant protein of interest, the nucleic acid sequence being extrachromosomal or chromosomally integrated and under the control of an inducible or constitutive promoter.

9. The CHO cell of claim 8, which cell produce higher levels of said recombinant protein of interest and/or has an increased cell-density as compared to a relevant control cell without disrupted expression of one or more endogenous proteins.

10. A method of producing a recombinant protein of interest, comprising
   culturing the CHO cell of claim 9 in a culture medium such that the protein of interest is expressed from the nucleic acid sequence;
   harvesting the recombinant protein of interest from the culture medium; and
   optionally, further purifying the harvested recombinant protein of interest.

11. A method for preparing the CHO cell of any one of claims 1 to 9, comprising the steps of
   modifying the CHO cell to knock-down or knock-out the endogenous gene or genes encoding one or more of TIMP1, NID1-1, NID1-2, BGN, and LGALS3BP; and
   optionally, transfecting the modified CHO cell with a nucleic acid sequence encoding a protein of interest.

12. The CHO cell of claim 1, which is selected from the group consisting of a CHO-K1, CHO-S and CHO DG44 cell.

* * * * *

SEQUENCE LISTING

<160> NUMBER OF SEQ ID NOS: 24

<210> SEQ ID NO 1
<211> LENGTH: 54
<212> TYPE: DNA
<213> ORGANISM: Artificial Sequence
<220> FEATURE:
<223> OTHER INFORMATION: DNA primer

<400> SEQUENCE: 1
ggaaaggacg aaacaccgcg gtcagtgacg cagcggagtt ttagagctag aaat    54

<210> SEQ ID NO 2
<211> LENGTH: 54
<212> TYPE: DNA
<213> ORGANISM: Artificial Sequence
<220> FEATURE:
<223> OTHER INFORMATION: DNA primer

<400> SEQUENCE: 2
ggaaaggacg aaacaccgcc ttctgcaact ccgacctgtt ttagagctag aaat    54

<210> SEQ ID NO 3
<211> LENGTH: 54
<212> TYPE: DNA
<213> ORGANISM: Artificial Sequence
<220> FEATURE:
<223> OTHER INFORMATION: DNA primer

```
<400> SEQUENCE: 3
ggaaaggacg aaacaccgca agttcacgtc tatccgtgtt ttagagctag aaat        54

<210> SEQ ID NO 4
<211> LENGTH: 54
<212> TYPE: DNA
<213> ORGANISM: Artificial Sequence
<220> FEATURE:
<223> OTHER INFORMATION: DNA primer

<400> SEQUENCE: 4
ggaaaggacg aaacaccgat ctccacgcgg ccctcacgtt ttagagctag aaat        54

<210> SEQ ID NO 5
<211> LENGTH: 54
<212> TYPE: DNA
<213> ORGANISM: Artificial Sequence
<220> FEATURE:
<223> OTHER INFORMATION: DNA primer

<400> SEQUENCE: 5
ggaaaggacg aaacaccgtg actgagcctg atccggagtt ttagagctag aaat        54

<210> SEQ ID NO 6
<211> LENGTH: 54
<212> TYPE: DNA
<213> ORGANISM: Artificial Sequence
<220> FEATURE:
<223> OTHER INFORMATION: DNA primer

<400> SEQUENCE: 6
ggaaaggacg aaacaccgtt gcggccgaga tggtcaagtt ttagagctag aaat        54

<210> SEQ ID NO 7
<211> LENGTH: 53
<212> TYPE: DNA
<213> ORGANISM: Artificial Sequence
<220> FEATURE:
<223> OTHER INFORMATION: DNA primer

<400> SEQUENCE: 7
ctaaaactcc gctgcgtcac tgaccgcggt gtttcgtcct ttccacaaga tat         53

<210> SEQ ID NO 8
<211> LENGTH: 53
<212> TYPE: DNA
<213> ORGANISM: Artificial Sequence
<220> FEATURE:
<223> OTHER INFORMATION: DNA primer

<400> SEQUENCE: 8
ctaaaacagg tcggagttgc agaaggcggt gtttcgtcct ttccacaaga tat         53

<210> SEQ ID NO 9
<211> LENGTH: 53
<212> TYPE: DNA
<213> ORGANISM: Artificial Sequence
<220> FEATURE:
<223> OTHER INFORMATION: DNA primer

<400> SEQUENCE: 9
ctaaaacacg gatagacgtg aacttgcggt gtttcgtcct ttccacaaga tat         53

<210> SEQ ID NO 10
<211> LENGTH: 53
```

```
<212> TYPE: DNA
<213> ORGANISM: Artificial Sequence
<220> FEATURE:
<223> OTHER INFORMATION: DNA primer

<400> SEQUENCE: 10
ctaaaacgtg agggccgcgt ggagatcggt gtttcgtcct ttccacaaga tat    53

<210> SEQ ID NO 11
<211> LENGTH: 53
<212> TYPE: DNA
<213> ORGANISM: Artificial Sequence
<220> FEATURE:
<223> OTHER INFORMATION: DNA primer

<400> SEQUENCE: 11
ctaaaactcc ggatcaggct cagtcacggt gtttcgtcct ttccacaaga tat    53

<210> SEQ ID NO 12
<211> LENGTH: 53
<212> TYPE: DNA
<213> ORGANISM: Artificial Sequence
<220> FEATURE:
<223> OTHER INFORMATION: DNA primer

<400> SEQUENCE: 12
ctaaaacttg accatctcgg ccgcaacggt gtttcgtcct ttccacaaga tat    53

<210> SEQ ID NO 13
<211> LENGTH: 22
<212> TYPE: DNA
<213> ORGANISM: Artificial Sequence
<220> FEATURE:
<223> OTHER INFORMATION: DNA primer

<400> SEQUENCE: 13
catggtggct actactgctt tt                                      22

<210> SEQ ID NO 14
<211> LENGTH: 22
<212> TYPE: DNA
<213> ORGANISM: Artificial Sequence
<220> FEATURE:
<223> OTHER INFORMATION: DNA primer

<400> SEQUENCE: 14
tcactgataa cctccagcaa gg                                      22

<210> SEQ ID NO 15
<211> LENGTH: 22
<212> TYPE: DNA
<213> ORGANISM: Artificial Sequence
<220> FEATURE:
<223> OTHER INFORMATION: DNA primer

<400> SEQUENCE: 15
ctcagcaggt gactgattgg ag                                      22

<210> SEQ ID NO 16
<211> LENGTH: 21
<212> TYPE: DNA
<213> ORGANISM: Artificial Sequence
<220> FEATURE:
<223> OTHER INFORMATION: DNA primer

<400> SEQUENCE: 16
```
gcacaaagca tcgaagtcct g                                      21

<210> SEQ ID NO 17
<211> LENGTH: 19
<212> TYPE: DNA
<213> ORGANISM: Artificial Sequence
<220> FEATURE:
<223> OTHER INFORMATION: DNA primer

<400> SEQUENCE: 17
tgggtaggga ctgctaccg                                         19

<210> SEQ ID NO 18
<211> LENGTH: 22
<212> TYPE: DNA
<213> ORGANISM: Artificial Sequence
<220> FEATURE:
<223> OTHER INFORMATION: DNA primer

<400> SEQUENCE: 18
tgccatccat tcttgcaact tc                                     22

<210> SEQ ID NO 19
<211> LENGTH: 20
<212> TYPE: DNA
<213> ORGANISM: Artificial Sequence
<220> FEATURE:
<223> OTHER INFORMATION: DNA primer

<400> SEQUENCE: 19
caaggtgggc atcaacgact                                        20

<210> SEQ ID NO 20
<211> LENGTH: 23
<212> TYPE: DNA
<213> ORGANISM: Artificial Sequence
<220> FEATURE:
<223> OTHER INFORMATION: DNA primer

<400> SEQUENCE: 20
atggccaaag tggatctatg caa                                    23

<210> SEQ ID NO 21
<211> LENGTH: 22
<212> TYPE: DNA
<213> ORGANISM: Artificial Sequence
<220> FEATURE:
<223> OTHER INFORMATION: DNA primer

<400> SEQUENCE: 21
agcctggagt atccttgggt ag                                     22

<210> SEQ ID NO 22
<211> LENGTH: 25
<212> TYPE: DNA
<213> ORGANISM: Artificial Sequence
<220> FEATURE:
<223> OTHER INFORMATION: DNA primer

<400> SEQUENCE: 22
gcatctaaaa tgttccagag gttgt                                  25

<210> SEQ ID NO 23
<211> LENGTH: 22
<212> TYPE: DNA
<213> ORGANISM: Artificial Sequence -continued

```
<220> FEATURE:
<223> OTHER INFORMATION: DNA primer

<400> SEQUENCE: 23
tggagtcatc atggacacac tc                                              22

<210> SEQ ID NO 24
<211> LENGTH: 23
<212> TYPE: DNA
<213> ORGANISM: Artificial Sequence
<220> FEATURE:
<223> OTHER INFORMATION: DNA primer

<400> SEQUENCE: 24
tcccatttgg tttctcaagg ttt                                             23
```